(12) United States Patent
Biering et al.

(10) Patent No.: US 6,540,960 B2
(45) Date of Patent: Apr. 1, 2003

(54) PROCESS FOR DISINFECTING INSTRUMENTS

(75) Inventors: Holger Biering, Grevenbroich (DE); Klaus-Peter Bansemir, Langenfeld (DE); Joerg Sorns, Duesseldorf (DE)

(73) Assignee: Henkel-Ecolab GmbH & Co. OHG (Henkel-Ecolab), Duesseldorf (DE)

( * ) Notice: Subject to any disclaimer, the term of this patent is extended or adjusted under 35 U.S.C. 154(b) by 18 days.

(21) Appl. No.: 09/319,711

(22) PCT Filed: Dec. 2, 1997

(86) PCT No.: PCT/EP97/06745
§ 371 (c)(1),
(2), (4) Date: Jun. 10, 1999

(87) PCT Pub. No.: WO98/25468
PCT Pub. Date: Jun. 18, 1998

(65) Prior Publication Data
US 2002/0182103 A1 Dec. 5, 2002

(30) Foreign Application Priority Data
Dec. 11, 1996 (DE) .......................... 196 51 415

(51) Int. Cl.⁷ .................. A61L 9/00; C11D 9/44
(52) U.S. Cl. .................. 422/28; 422/29; 510/101
(58) Field of Search ............ 422/28, 29; 510/101

(56) References Cited

U.S. PATENT DOCUMENTS

| | | | | |
|---|---|---|---|---|
| 3,630,921 A | * | 12/1971 | Disch et al. ............ 252/95 |
| 3,753,914 A | * | 8/1973 | Berth et al. ............ 252/95 |
| 3,816,319 A | * | 6/1974 | Sarot et al. ............ 252/99 |
| 3,956,156 A | * | 5/1976 | Osband et al. ............ 252/99 |
| 4,110,242 A | * | 8/1978 | Hase et al. ............ 252/186 |
| 4,160,833 A | * | 7/1979 | Diel ............ 424/249 |
| 4,344,955 A | * | 8/1982 | Niemers et al. ............ 424/271 |
| 4,378,300 A | * | 3/1983 | Gray ............ 252/99 |
| 4,664,837 A | * | 5/1987 | Gray ............ 252/99 |
| 4,695,397 A | * | 9/1987 | Sommer et al. ............ 252/99 |
| 5,021,182 A | * | 6/1991 | Jentsch ............ 252/95 |
| 5,370,815 A | * | 12/1994 | Kessler ............ 252/106 |

FOREIGN PATENT DOCUMENTS

| | | |
|---|---|---|
| DE | 20 26 240 | 12/1971 |
| DE | 26 55 599 | 6/1978 |
| DE | 27 01 133 | 7/1978 |
| DE | 28 15 400 | 10/1979 |
| DE | 36 15 787 | 11/1987 |
| GB | 1 337 858 | 11/1973 |
| GB | 1 566 671 | 5/1980 |
| GB | 1 571 357 | 7/1980 |
| GB | 2 268 879 | 1/1994 |
| WO | WO95/02330 | 1/1995 |
| WO | WO95/20876 | 8/1995 |

OTHER PUBLICATIONS

J.Prakt.Chem. No. 334, (1992) XP002062685 pp. 293–297.
Hygiene und Medizin, vol. 21, (1996) pp. 375–376.

* cited by examiner

Primary Examiner—Robert J. Warden, Sr.
Assistant Examiner—Imad Soubra

(57) ABSTRACT

A process useful for disinfecting medical instruments is presented involving reacting a hydrogen peroxide donor with an N-acyl compound in an aqueous medium having a pH of 9 to 11 to form an acylated hydrogen peroxide preparation, reducing the pH of the acylated hydrogen peroxide preparation to pH 7 to 9; and contacting the acylated hydrogen peroxide preparation with a medical instrument. The process provides good antimicrobial activity with little corrosion. The process is effective against mycobacteria.

21 Claims, No Drawings

PROCESS FOR DISINFECTING INSTRUMENTS

This application is filed under 35 U.S.C. 371 and based on PCT/EP97/06745, filed Dec. 2, 1997.

BACKGROUND OF THE INVENTION

1. Field of the Invention

This invention relates to a process for disinfecting instruments, more especially medical instruments, using aqueous peroxidic formulations.

2. Discussion of Related Art

Over the years, the chemical disinfection of instruments using aqueous formulations has been the subject of numerous studies in which various antimicrobial agents have been proposed for disinfection. Preparations based on aldehydes have been the most widely used in practice, although preparations containing quaternary ammonium compounds, phenols, alcohols and other disinfecting agents have also been used. By contrast, preparations based on peroxidic agents, more especially peracetic acid, have acquired very little significance for this particular application. One of the main reasons for this lies in the poor stability of such aqueous preparations in storage. In view of the broad antimicrobial activity of peroxides, there has been no shortage of attempts to overcome the disadvantage of their poor stability in storage. For example, it is proposed in DE-OSS 26 55 599 and 28 15 400 to prepare the aqueous preparations required for disinfection just before use from more stable precursors, namely from sodium perborate and anhydrides. According to DE-OS 27 01 133, the aqueous preparations are obtained from compounds which release hydrogen peroxide and aromatic acyloxycarboxy acids. However, only a few of these compounds give disinfecting solutions with sufficiently broad activity, in addition to which these acylating agents can only be stored for a limited period in admixture with the necessary inorganic peroxides on account of decomposition reactions. "Sekusept Pulver (Sekusept Powder)" is a commercially available product which dissolves in water to form a disinfecting preparation by reaction of sodium perborate with tetraacetyl ethylenediamine (TAED). This product, which is based on an N-acyl compound, has a broad action spectrum and is stable in storage. Although a high standard in the disinfection of medical instruments has already been achieved in this way, more work is being done to improve the peroxidic systems in order to eliminate the gaps which still exist in the action spectrum and disadvantages in use. For example, it is proposed in DE-OS 36 15 787 to use the magnesium salt of monoperoxyphthalic acid instead of inorganic hydrogen peroxide donors in the production of such preparations. However, the use of this organic peroxide involves considerably greater outlay on equipment compared with the use of the storage stable and inexpensive inorganic peroxides. Accordingly, the problem addressed by the present invention was to achieve an improvement in disinfection systems based on inorganic peroxides and N-acyl compounds. One of the associated problems to be solved in this regard was to develop a disinfection process which would even enable mycobacteria to be safely disinfected. In addition, easy handling, high stability in storage and only a very slight tendency towards corrosion would be guaranteed.

It has now been found that a significant improvement in the known disinfection systems based on inorganic hydrogen peroxide donors and N-acyl compounds can be achieved by a remarkably simple measure.

DESCRIPTION OF THE INVENTION

The present invention relates to a process for disinfecting medical instruments by treating the instruments with a microbicidally active aqueous preparation in which the following two steps A and B are successively carried out in the production of the microbicidal preparation:

A: reacting hydrogen peroxide or peroxidic compounds which form hydrogen peroxide in water in an aqueous alkaline medium with N-acyl compounds which are capable under these conditions of acylating hydrogen peroxide, B: reducing the pH value of the preparation obtained in step A and optionally diluting the preparation so that a pH value in the range from 7 to 9 and preferably in the range from 7.5 to 8.5 is established in the preparation used for disinfection.

Through the comparatively simple measure of subsequently reducing the pH value, which can be done with any of the usual acids, a considerable increase in antimicrobial activity coupled with only a very slight tendency towards corrosion is achieved without losing any of the advantages of the known process.

In the production of the microbicidally active aqueous preparation, step A of the process according to the invention starts out from hydrogen peroxide or from peroxidic compounds which immediately release hydrogen peroxide when dissolved in water. These peroxidic compounds can be adducts of hydrogen peroxide with various carriers, which are sometimes also referred to as perhydrates, for example urea perhydrate, sodium citrate perhydrate or sodium carbonate perhydrate ($Na_2CO_3 \times 1.5\ H_2O_2$), which normally is also referred to as sodium percarbonate. True inorganic peroxo compounds which hydrolyze spontaneously in water, for example the sodium perborates, for example sodium perborate monohydrate and sodium perborate tetrahydrate, are also suitable. By contrast, organic peroxo compounds in which the peroxo group is directly attached to carbon are unsuitable. Sodium percarbonate and the mono- and tetrahydrates of sodium perborate are particularly preferred for the purposes of the process according to the invention, the monohydrate being most particularly preferred. Several per compounds may also be used at one and the same time.

In principle, suitable N-acyl compounds for the reaction in step A are any compounds of this group which have also been described in detergent chemistry as so-called bleach activators for reaction with hydrogen peroxide in alkaline wash liquors. Suitable N-acyl compounds are, in particular, those which contain another keto group at the nitrogen which carries the acyl group and/or in which the nitrogen is part of a heterocyclic ring system. Examples of suitable N-acyl compounds are the polyacylated alkylenediamines, such as for example tetraacetyl ethylenediamine, acylated glycol urils, above all tetraacetyl glycol uril, N-acylated hydantoins, hydrazides, triazoles, triazines, urazoles, diketopiperazines, sulfuryl amides, lactams and cyanurates. Tetraacetyl ethylenediamine (TAED), tetraacetyl glycol uril (TAGU) and 1,5-diacetyl-2,4-dioxohexahydro-1,3,5-triazine (DADHT) are preferred for the purposes of the process according to the invention, tetraacetyl ethylenediamine being particularly preferred. Several N-acyl compounds may of course also be used at one and the same time.

The reaction of the compound yielding hydrogen peroxide and the N-acyl compound in step A is carried out by introducing the two compounds into water successively or, preferably, at the same time. If the peroxidic compound, for example sodium percarbonate and sodium perborate, has sufficient alkalinity, there may be no need to add alkalizing agents. Otherwise, compounds showing an alkaline reaction, preferably inorganic salts, for example sodium carbonate, alkali metal phosphates or alkali metal borates, will have to be added to establish a pH value which, even after the reaction has been completed, is still in the alkaline range, preferably above 8.5 and more preferably between 9 and 11. The ratio of the hydrogen peroxide donor to the N-acyl compound is preferably selected so that 0.5 to 10 moles and preferably 1 to 5 moles of hydrogen peroxide are available per mole of reactive acyl groups in the N-acyl compound. Accordingly, about 0.1 to about 1% by weight and, more particularly, about 0.2 to about 0.6% by weight of peroxidic compounds and 0.1 to about 1% by weight and, more particularly, about 0.2 to about 0.5% by weight of N-acyl compound, based on the total weight of the preparation in step A, are preferably used.

The reaction between hydrogen peroxide and the N-acyl compound in step A is a time reaction which is dependent on the concentration of the reactants, the reactivity of the N-acyl compound, the pH value of the solution and the temperature. The reaction can be accelerated by increasing the concentrations and by increasing the temperature. The reaction is preferably carried out at a temperature in the range from about 10 to about 45° C., temperatures around or just above room temperature being particularly suitable. With particularly suitable N-acyl compounds, the reaction takes place so quickly that at least 50% of the N-acyl compound has reacted off after 1 to 20 minutes and, more particularly, after 2 to 10 minutes under the preferred conditions.

Lowering of the pH value in step B is preferably not initiated until more than 50%, preferably more than 70% and, more preferably, more than 80% of the N-acyl compound has reacted off in step A. The pH value is lowered by adding compounds showing an acidic reaction, more especially inorganic or organic acids or salts with an acidic reaction in suitable quantities. In addition, the preparation may if necessary be diluted in step B, so that the peroxidic active substances formed in step A reach the correct concentration for the disinfecting process. The quantity of acid or acidic compound is selected so that a pH value in the range from 7 to 9 and, more particularly, in the range from 7.5 to 8.5 is established in the solution intended for the disinfection process. Particularly suitable acids for lowering the pH value in step B are, for example, phosphoric acid, acetic acid, citric acid and—generally—water-soluble organic acids. Acidic phosphates, such as $NaH_2PO_4$, and hydrogen sulfates are mentioned as examples of suitable salts showing an acidic reaction. Phosphoric acid, acetic acid and citric acid are particularly preferred for step B of the process according to the invention, phosphoric acid being most particularly preferred.

Other auxiliaries and additives may be added to the preparation in step A and/or step B if this is of advantage for the use according to the invention for disinfecting medical instruments. Other auxiliaries which may be used in step A are, preferably, surfactants, alkalizing agents, complexing agents for water hardness, complexing agents for heavy metal ions and water-soluble inorganic salts. Corrosion inhibitors and surfactants are preferably used as auxiliaries in step B. The quantity in which auxiliaries such as these are used in the preparations may vary within very wide limits, depending on the intended effect. It is normally not more than about 3% by weight and is preferably between about 0.001 and about 1% by weight, based on the preparation as a whole.

Suitable surfactants are both anionic and nonionic surfactants although cationic surfactants and amphoteric surfactants may also be used. Anionic surfactants and nonionic surfactants and optionally mixtures of several surfactants from these two classes are preferably used as surfactants in step A. Suitable anionic surfactants are, in particular, alkyl benzenesulfonates, alkyl sulfates, i.e. the salts of sulfuric acid semiesters of long-chain alcohols, alkyl ether sulfates, i.e. salts of sulfuric acid semiesters of long-chain alkoxylated, more especially ethoxylated, alcohols, alkane sulfonates and olefin sulfonates. The anionic surfactants are preferably used in the form of sodium salts. Alkoxylated long-chain alcohols are mentioned as particularly suitable nonionic surfactants. The alcohols alkoxylated with ethylene oxide and the types alkoxylated with ethylene oxide and a small quantity of propylene oxide are preferred. Other preferred nonionic surfactants which may be used in particular when low foaming is an important factor are the so-called end-capped alkoxylation products which are obtainable from the nonionic surfactants mentioned above by etherification of the terminal hydroxyl group with short-chain alcohols.

In principle, the surfactants used in step B may be the same as those as described for step A although there is a greater preference for nonionic surfactants in step B. If the surfactants are made up together with the acids required for lowering the pH value in step B, the acid-stable surfactants are particularly appropriate for this formulation.

Sodium triphosphate is mentioned as a particularly suitable complexing agent for water hardness although other polyphosphates, salts of nitrilotriacetic acid and salts of organic polycarboxylic acids, for example citric acid, or of polymeric polycarboxylic acids, for example acrylic acid/maleic acid copolymers, may also be used for this purpose. Sodium tripolyphosphate, which also acts as an alkalizing agent, is particularly preferred.

Suitable complexing agents for heavy metal ions which have a decomposing effect on peroxidic compounds are, above all, aminopolycarboxylic acids and salts thereof, for example ethylenediamine tetraacetic acid, but especially aminopolyphosphonic acids, such as ethylenediamine tetramethylene phosphonic acid, or even hydroxyethane diphosphonic acid and salts thereof.

Water-soluble salts are capable of acting as fillers or builders, like sodium sulfate for example, providing they do not also have an alkalizing effect, like sodium carbonate and sodium silicate for example. Suitable corrosion inhibitors are, in particular, alkyl phosphonic acids, among which octane phosphonic acid is particularly preferred. Dyes, perfume and solubilizing additives are mentioned as other possible auxiliaries.

The process according to the invention may readily be carried out by combining all the substances to be used in step A and all those to be used in step B into single products in the required quantity so that steps A and B may readily be carried out by dissolving the respective products in the necessary quantity of water (step A) and adding the preparation formed in step A after a predetermined time (step B). These products prepared in advance for steps A and B may be solid or liquid, depending on the aggregate state of the substances to be used. The product intended for step A is preferably a powder-form mixture of the individual substances, the particle form preferably being selected so that the individual substances dissolve sufficiently quickly and are thus available for the reaction. So far as the storage stability of the powder-form product itself is concerned, it can be useful to use individual substances or several of the substances, more especially the N-acyl compounds and/or peroxidic compound, in granulated form or in coated form. However, instead of a powder, the product intended for step A may also be made up in a more compact form, for example as a tablet, providing steps are taken, for example by adding suitable disintegrating agents, to ensure that these tablets dissolve sufficiently quickly in water.

A solid formulation is also possible for the product intended for step B although, in this case, a liquid formulation may equally well be selected by virtue of the smaller stability problems in storage. Concentrated aqueous solutions are particularly suitable. This product, too, may advantageously be formulated in portions, for example to enable dosage requirements to be more easily satisfied.

A product intended for carrying out step A by dissolution in water may have in particular the following composition:

- 5 to 40% by weight, preferably 10 to 30% by weight of solid inorganic per compound,
- 5 to 30% by weight, preferably 10 to 20% by weight of powder-form TAED,
- 20 to 50% by weight, preferably 30 to 45% by weight of sodium triphosphate,
- 0 to 15% by weight, preferably 1 to 10% by weight of surfactant and balance to 100% by weight soluble inorganic salt and optionally other auxiliaries.

It is dissolved in water in a quantity of preferably 1 to 10% by weight.

A product suitable for addition in step B may have in particular the following composition:

- 40 to 80% by weight, preferably 55 to 65% by weight of concentrated phosphoric acid,
- 0.01 to 5% by weight, preferably 0.05 to 0.5% by weight of corrosion inhibitor,
- 0 to 10% by weight, preferably 0.5 to 4% by weight of surfactant, balance to 100% by weight water and optionally other auxiliaries.

In the process according to the invention, the actual disinfection of medical instruments is carried out by introducing the instruments into the ready-to-use solution of the peroxidic active substances resulting from step B so that they are completely wetted by this solution. The immersion time depends upon the concentration of the disinfecting solution and also to a very large extent on the germ spectrum to be controlled. It is particularly worth mentioning that not only can the usual germ spectrum of bacteria and fungi be eliminated by the process according to the invention, the particularly resistant mycobacteria can also be destroyed. The disinfecting solution prepared in step B remains stable for a sufficiently long time and has a negligible corrosive effect on metal instruments.

EXAMPLES

1. Preparation of the Disinfecting Solution 2 g of a powder-form mixture consisting of 20% by weight of sodium perborate monohydrate, 15% by weight of TAED powder, 40% by weight of sodium triphosphate, 15% by weight of sodium carbonate, 2% by weight of alkyl benzenesulfonate and 8% by weight of sodium sulfate were dissolved in 100 ml of tap water at room temperature. After 15 minutes, 0.5 g of an acid mixture consisting of 60.0% by weight of concentrated phosphoric acid, 0.2% by weight of octane phosphonic acid, 0.4% by weight of fatty alcohol ethoxylate (Dehypon LS 54®, Henkel KGaA), 0.4% by weight of sodium cumene sulfonate and 39.0% by weight of water was added to the solution formed. The resulting solution had a pH value of 7.9 and, without further dilution, was tested for its effectiveness against mycobacteria and for its corrosive effect.

2. Testing of Effectiveness Against Mycobacteria

The "Quantitative Suspensionsversuch mit Mycobakterium terrae für die Prüfung von Instrumentendesinfektionsmitteln (Quantitative Suspension Test with Mycobacterium terrae for the Testing of Instrument Disinfectants)" (Hygiene und Medizin 21, 375-376, 1996) was used as the test method. In this test, the destruction of the test germ is quantitatively determined as a logarithmic reduction factor to the water used as control. Both the disinfecting solution prepared in accordance with 1) (b) and, for example comparison, a corresponding solution whose pH value had not been reduced (a) were tested.

| | Reduction factor after an immersion time of | |
|---|---|---|
| Test solutions | 30 mins. | 60 mins. |
| a) Powder mixture with acid mixture (2 g in 100 ml of water) | 0.14 | 0.38 |
| b) Powder mixture (2 g in 100 ml of water) plus acid mixture (0.5 in 100 ml of water) | 5.07 | ≧5.21 |
| Water control (living control) | 6.07 | 6.21 |

After only 30 minutes, totally adequate effectiveness was achieved with preparation (b) according to the invention whereas reference solution (a) was virtually ineffective, even after 60 minutes.

3. Testing of Corrosive Effect

The corrosive behavior of the disinfecting solution (b) intended for the process according to the invention was tested by completely immersing degreased iron nails in the test solution. Evaluation was carried out after 8 hours by comparison with untreated nails and nails stored in tap water. Evaluation was carried out on the following scale after visual assessment of deposits, residues and visible signs of corrosion:

0=no corrosion
1=slight corrosion
2=medium corrosion
3=serious corrosion

In this case, too, both the disinfecting solution (b) prepared in accordance with 1) and—for comparison—a corresponding solution (a) whose pH value had not been lowered were tested. The tap water which had been used to prepare the test solutions was used on its own for further comparison. The following results were obtained:

| Test solutions | Evaluation |
|---|---|
| a) Powder mixture without acid mixture (2 g in 100 ml of water) | 0 |
| b) Powder mixture (2 g of 100 ml of water) plus acid mixture (0.5 g in 100 ml of water) | 0 |
| Standard sample (water) | 3 |

4. Instrument Disinfection

An instrument tank was filled with 20 liters of cold tap water. To prepare the disinfecting solution, 400 g of the powder-form mixture were first stirred in and, after 15 minutes, 100 g of the acid mixture were added while stirring in accordance with Example 1.

The instruments to be cleaned and disinfected were introduced into and completely wetted with the disinfecting solution. After an immersion time of 60 minutes, the instruments were removed from the solution and rinsed with drinking water.

What is claimed is:

1. A method for disinfecting medical instruments comprising:
   (a) reacting a hydrogen peroxide donor with an N-acyl compound in an aqueous medium having a pH of 9 to 11, to form an acylated hydrogen peroxide preparation;
   (b) reducing the pH of said acylated hydrogen peroxide preparation to pH 7 to 9;
   (c) contacting said pH reduced and acylated hydrogen peroxide preparation with a medical instrument suspected of contamination with mycobacteria; and
   (d) significantly reducing the population of mycobacteria on the medical instrument.

2. The method of claim 1 wherein 0.5 to 10 moles of the hydrogen peroxide donor are used for each mole of N-acyl compound.

3. The method of claim 1 wherein 1 to 5 moles of the hydrogen peroxide donor are used for each mole of N-acyl compound.

4. The method of claim 1 wherein the acylated hydrogen peroxide preparation comprises 0.1 to 1 percent by weight hydrogen peroxide donor and 0.1 to 1 percent by weight N-acyl compound.

5. The method of claim 4 wherein the acylated hydrogen peroxide preparation comprises 0.2 to 0.6 percent by weight hydrogen peroxide donor and 0.2 to 0.5 percent by weight N-acyl compound.

6. The method of claim 1 wherein the reaction of step (a) occurs at a temperature of from 10 to 45° C.

7. The method of claim 1 wherein the reaction of step (a) is at least 50 percent complete within 1 to 20 minutes.

8. The method of claim 7 wherein the reaction of step (a) is at least 50 percent complete within 2 to 10 minutes.

9. The method of claim 1 wherein the pH reduction of step (b) is initiated after the reaction of step (a) is more than 50 percent complete.

10. The method of claim 9 wherein the pH reduction of step (b) is initiated after the reaction of step (a) is more than 70 percent complete.

11. The method of claim 10 wherein the pH reduction of step (b) is initiated after the reaction of step (a) is more than 80 percent complete.

12. The method of claim 1 further comprising dissolving a solid mixture of an inorganic peroxide and an N-acyl compound in water prior to the reaction of step (a).

13. The method of claim 1 further comprising adding an alkalizing agent in step (a) for pH adjustment of the aqueous medium.

14. The method of claim 1 wherein the hydrogen peroxide donor is hydrogen peroxide or a peroxide compound capable of forming hydrogen peroxide in water.

15. The method of claim 1 wherein the hydrogen peroxide donor is selected from the group consisting of sodium perborate monohydrate, sodium perborate tetrahydrate and sodium percarbonate.

16. The method of claim 1 wherein the N-acyl compound is selected from the group consisting of tetraacetyl glycol uril, tetraacetyl ethylenediamine, and diacetyl hexahydrotriazine dione.

17. The method of claim 1 wherein the pH reduction of step (b) is effected by the addition of phosphoric acid, acetic acid or citric acid.

18. The method of claim 1 wherein the pH in step (b) is reduced to pH 7.5 to 8.5.

19. The method of claim 1 comprising contacting said acylated hydrogen peroxide preparation with mycobacteria on medical instruments.

20. A method for disinfecting medical instruments comprising:
   (a) dissolving in water 1 to 10 percent by weight of a powder-form mixture comprising:
      (1) 5 to 40 percent by weight of a solid inorganic per-compound;
      (2) 5 to 30 percent by weight of power-form tetraacetyl ethylenediamine;
      (3) 20 to 50 percent by weight of sodium triphosphate;
      (4) 0 to 15 percent by weight of surfactant; and the balance to 100 percent by weight of soluble inorganic salt and other auxiliaries to form an acylated hydrogen peroxide preparation;
   (b) reducing the pH of said acylated hydrogen peroxide preparation to pH 7.5–8.5 by adding:
      (1) 40 to 80 percent by weight of concentrated phosphoric acid;
      (2) 0.01 to 5 percent by weight of corrosion inhibitor;
      (3) 0 to 10 percent by weight of surfactant; and the balance to 100 percent by weight water and other auxiliaries;
   (c) contacting said pH reduced and acylated hydrogen peroxide preparation with a medical instrument suspected of contamination with mycobacteria; and
   (d) significantly reducing the population of mycobacteria on the medical instrument.

21. The method of claim 20 comprising:
   (a) dissolving in water 1 to 10 percent by weight of a powder-form mixture comprising:
      (1) 10 to 30 percent by weight of a solid inorganic per-compound;
      (2) 10 to 20 percent by weight of powder-form tetraacetyl ethylenediamine;
      (3) 30 to 45 percent by weight of sodium triphosphate;
      (4) 1 to 10 percent by weight of surfactant; and the balance to 100 percent by weight of soluble inorganic salt and other auxiliaries to form an acylated hydrogen peroxide preparation;
   (b) reducing the pH of said acylated hydrogen peroxide preparation to pH 7.5–8.5 by adding:
      (1) 50 to 65 percent by weight of concentrated phosphoric acid;
      (2) 0.05 to 0.5 percent by weight of corrosion inhibitor;
      (3) 0.5 to 4 percent by weight of surfactant; and the balance to 100 percent by weight water and other auxiliaries; and
   (c) contacting said acylated hydrogen peroxide preparation with a medical instrument.

* * * * *